(12) United States Patent
Liu et al.

(10) Patent No.: US 6,861,106 B2
(45) Date of Patent: Mar. 1, 2005

(54) DICHROIC DYE, COMPOSITION THEREOF, AND LIQUID CRYSTAL COMPOSITION AND LIQUID CRYSTAL DISPLAY ELEMENT CONTAINING THE SAME

(75) Inventors: Shih-Hsien Liu, Taipei (TW); Yang-Chu Lin, Hsinchu (TW); Woan-Shiow Tzeng, Hsinchu (TW); Jie-Hwa Ma, Hainchu (TW); Kung-Lung Cheng, Hainchu (TW); Long-Li Lai, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 10/443,808

(22) Filed: May 23, 2003

(65) Prior Publication Data

US 2004/0135117 A1 Jul. 15, 2004

(30) Foreign Application Priority Data

Dec. 27, 2002 (TW) ........................ 91137651 A

(51) Int. Cl.$^7$ ............... C09K 19/36; C09B 1/50; C09B 29/00; C09B 56/04; C07D 285/08
(52) U.S. Cl. ............... 428/1.1; 252/299.1; 252/299.68; 534/688; 534/689; 544/392; 544/402; 552/243; 548/128; 548/129; 548/130
(58) Field of Search ............... 428/1.1; 252/299.1, 252/299.68; 534/688, 689; 544/392, 402; 548/128, 129, 130; 552/243

(56) References Cited

FOREIGN PATENT DOCUMENTS

| JP | 7-252423 | * 10/1995 |
| JP | 10-231436 | * 9/1998 |

OTHER PUBLICATIONS

English translation by computer for JP 10–231436, http://www4.ipdl.jpo.go.jp/Tokujitu/PAJdetail.ipdl?N0000=60&N0120=01&N2001=2&N3001=H10–231436.*

English translation by computer for JP 07–252423, http://www4.ipdl.jpo.go.jp/Tokujitu/PAJdetail.ipdl?N0000=60&N0120=01&N2001=2&N3001=H07–252423.*

Lai et al., "N,N–Disubstituted aminophenylazo–4–benzoates: preparation, mesogenic study, structure determination and molecular modeling", Liquid Crystals, 2001, vol. 28, No. 10, pp. 1513–1518.*

Matsui et al., Synthesis of perfluorobutyl–substituted ester–diazo dyes and their application to guest–host liquid crystal displays Liquid Crystals, 2002, vol. 29, No. 5, pp. 707–712.*

* cited by examiner

Primary Examiner—Shean C. Wu
(74) Attorney, Agent, or Firm—Sughrue Mion, PLLC

(57) ABSTRACT

Dichroic dyes, dichroic dye compositions, and liquid crystal composition and liquid crystal display element containing the dichroic dyes. The dichroic dye has increased solubility and stability.

24 Claims, 6 Drawing Sheets

DICHROIC DYE, COMPOSITION THEREOF, AND LIQUID CRYSTAL COMPOSITION AND LIQUID CRYSTAL DISPLAY ELEMENT CONTAINING THE SAME

BACKGROUND OF THE INVENTION

1. Field of the Invention

The present invention relates to a novel dichroic dye compound, composition thereof, and the liquid crystal composition and the liquid crystal display element containing the compound of the invention. In particular, the dichroic dye compound of the invention can be used in photoelectric products, for example, liquid crystal displays, especially reflective liquid crystal displays.

2. Description of the Related Art

There is an increasing need for reflective liquid crystal displays for use in information products, such as E-books and PDAs, because they consume low electric energy and are thin and light. Currently, the guest-host display mode is applied in reflective liquid crystal displays, dye being "guest" and liquid crystal being "host". The liquid crystal display effects are generated by the anisotropically optical absorption by dichroic dye which is dissolved in the mixture of nematic liquid crystal and an optically active substance. This display mode employs absorption or no absorption for visible light by dye, exhibits bright and dark corresponding to the variation of electric field and may replace reflectors. The view angle of this type of reflective liquid crystal display is improved and the brightness is also increased. When used, only environmental light is required, but not back light, therefore electric consumption can be greatly reduced.

In guest-host display mode, dichroic dyes are used and must exhibit good dichroism, which can be quantified by the orientational order parameter ($S_D$) or dichroic ratio (N) of the dye molecules. The contrast is higher when the values of N and $S_D$ are higher. Moreover, the dye molecules in the display devices tend to deteriorate due to long term exposure to irradiation of back light or environmental light (such as sun light), and the display quality is affected adversely. Accordingly, it is desirable for the dyes to have good photostability and heat stability for enhanced durability. Furthermore, the solubility of dichroic dye in liquid crystal is generally 1%~10% based on the weight of liquid crystal. The dichroic dye rotates as the liquid crystal rotates in accordance with the increase of applied electric voltage. To increase the contrast of the display, an increase in solubility and load of dichroic dye in liquid crystal is desirable to fulfill the prerequisite of avoiding reduced brightness and increased threshold electric voltage.

However, few conventional dichroic dyes meet all the requirements mentioned above. Conventional dichroic dyes, those which meet the basic requirements for dichroism and coloration, often have poor processability because of poor solubility or short product life because of poor photostability.

For example, the photostability and heat stability of general azo dyes are poor, but those of anthraquinone dyes are relatively stable due to the hydrogen bond between molecules. The mono-azo dye having heterocyclic julolidine or thiazole group has relatively high photostability, but reduced solubility. U.S. Pat. No. 4,304,683 discloses an anthraquinone dye having a long linear or branched soft hydrocarbyl group, which has an asymmetric molecular structure, but the solubility is poor. In EP 0098522, the soft hydrocarbyl group is replaced by dialkylamino group and this can improve solubility of the dichroic dyes. *Liquid Crystals,* 2002, 29, pp707–712 reports the solubility of ester-disazo dyes can be improved by the introduction of multi-fluorine atoms.

Therefore, there is still a need for dichroic dyes with high solubility and stability.

SUMMARY OF THE INVENTION

Accordingly, an object of the invention is to provide a compound, which is a novel azo compound having a heterocyclic group and various functional groups and used as a yellow, orange, or red dichroic dye, depending on the structure of molecular moiety. Such azo compound dichroic dye has good light stability in addition to excellent solubility.

Another object of the invention is to provide a compound, which is a novel anthraquinone compound having a side chain group with multi-fluorine atoms and is used as a blue dichroic dye. Such anthraquinone compound dichroic dye has good solubility in addition to excellent light stability.

Still another object of the invention is to provide a dichroic dye composition, in which, a black dichroic dye composition, comprising the above mentioned dichroic dyes.

Still another object of the invention is to provide a dichroic dye liquid crystal composition comprising the above mentioned dichroic dyes or dichroic dye composition.

The present dichroic dye has good light stability, heat stability, and solubility and thus advantageously imparts liquid crystal display devices increased durability.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The present invention provides a compound having formula

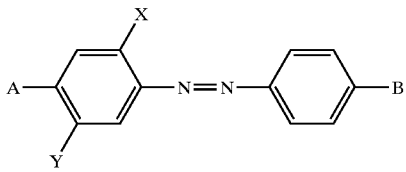

(I)

wherein

A is

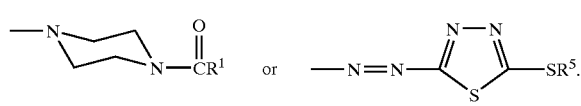

When A is

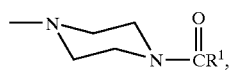

B is —COOR$^2$ or —CHC(CN)COOR$^4$ and X and Y are both hydrogen, wherein R$^1$, R$^2$, and R$^4$ are each independently a C$_{1-10}$ alkyl group which may be substituted by one or more fluorine atoms.

When A is

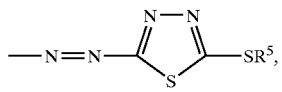

B is —NR$^6$R$^7$ and X and Y are different and X is a C$_{1-4}$ alkyl group, and Y is Cl, Br, I, a C$_{1-4}$ alkyl group, —OCH$_3$, or —OC$_2$H$_5$ or X and Y, being the same, are Cl, Br, I, a C$_{1-4}$ alkyl group, —OCH$_3$, or —OC$_2$H$_5$, wherein R$^5$ is —CH$_3$ or —C$_2$H$_5$, and R$^6$ and R$^7$ are each independently a C$_{1-10}$ alkyl group, —CH$_2$CH$_2$(CF$_2$)$_m$F,

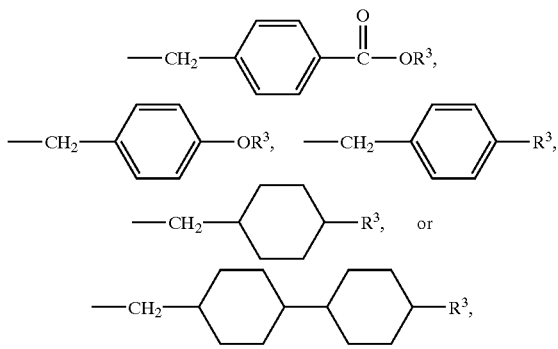

wherein m is an integer of 1 to 10 and R$^3$ is an C$_{1-4}$ alkyl group.

In an embodiment of the present invention, the compound has formula (II) and is a yellow dichroic dye:

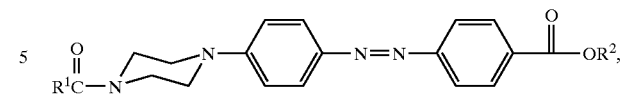

(II)

wherein R$^1$ and R$^2$ are defined as the above. Preferably, R$^1$ is a C$_{2-8}$ alkyl group which may be substituted by one or more fluorine atoms, and more preferably, R$^1$ is —C$_5$H$_{11}$. Preferably, R$^2$ is a C$_{2-8}$ alkyl group which may be substituted by one or more fluorine atoms, and, more preferably, R$^2$ is —C$_4$H$_9$.

In another embodiment of the present invention, the compound has formula (III) and is an orange dichroic dye:

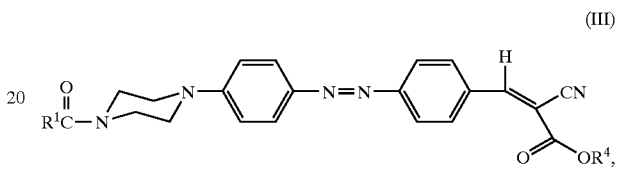

(III)

wherein R$^1$ and R$^4$ are each independently a C$_{1-10}$ alkyl group which may be substituted by one or more fluorine atoms, as mentioned above. Preferably, R$^1$ is a C$_{2-8}$ alkyl group which may be substituted by one or more fluorine atoms, and more preferably, R$^1$ is —C$_5$H$_{11}$. Preferably, R$^4$ is a C$_{2-8}$ alkyl group which may be substituted by one or more fluorine atoms, and, more preferably, R$^4$ is —C$_4$H$_9$.

In still another embodiment of the present invention, the compound has formula (IV) and is a red dichroic dye:

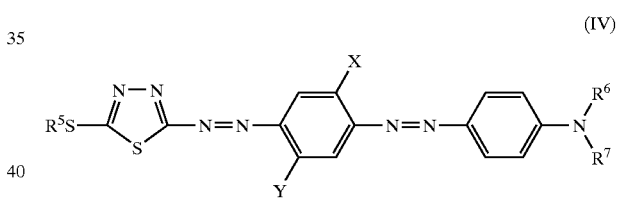

(IV)

wherein X, Y, R$^5$, R$^6$, and R$^7$ are defined as mentioned above. X is preferably a C$_{1-4}$ alkyl group, more preferably —CH$_3$. Y is preferably a C$_{1-4}$ alkyl group, more preferably —CH$_3$. R$^6$ is preferably a C$_{1-2}$ alkyl group, more preferably —CH$_3$. R$^7$ is preferably a C$_{1-10}$ alkyl group, more preferably —C$_8$H$_{17}$.

The synthesis of azo compound dichroic dye of the present invention is described as follows.

Figure 1A:
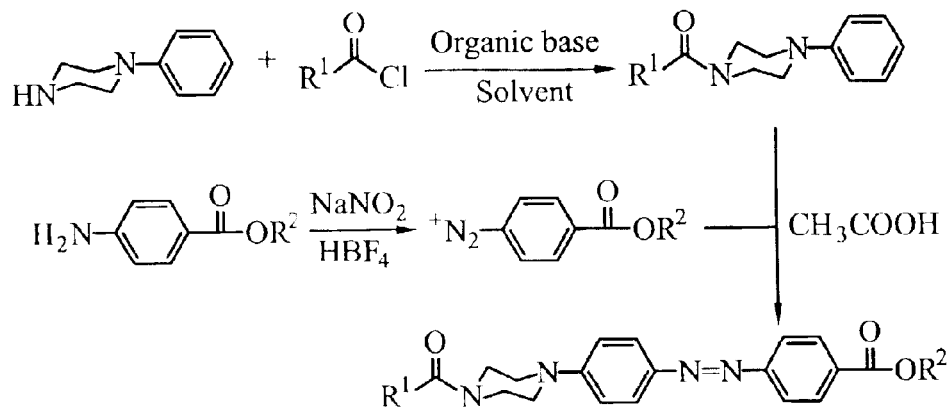
FIGS. 1a~1d briefly show synthesis flows for preparing a yellow, orange, red, and blue dichroic dye of the present invention, respectively.

Referring to FIG. 1a for the preparation of the yellow dichroic dye of the present invention, R$^1$ and R$^2$ are defined as mentioned above. Phenylpiperazine and alkanoyl chloride are dissolved in a non-polar solvent, such as methylene chloride. An organic base, such as Et$_3$N, is added to the resulting solution in an ice bath to form a phenylpiperazine derivative. Separately, 4-aminobenzoic acid alkyl ester reacts with sodium nitrite and HBF4 at 0° C. to form a diazonium salt. Then, the diazonium salt and the above phenylpiperazine derivative are allowed to react in acetic acid at room temperature, forming an azobenzoic acid alkyl ester having a piperazinyl group as shown in FIG. 1a, a yellow dichroic dye.

Figure 1B:
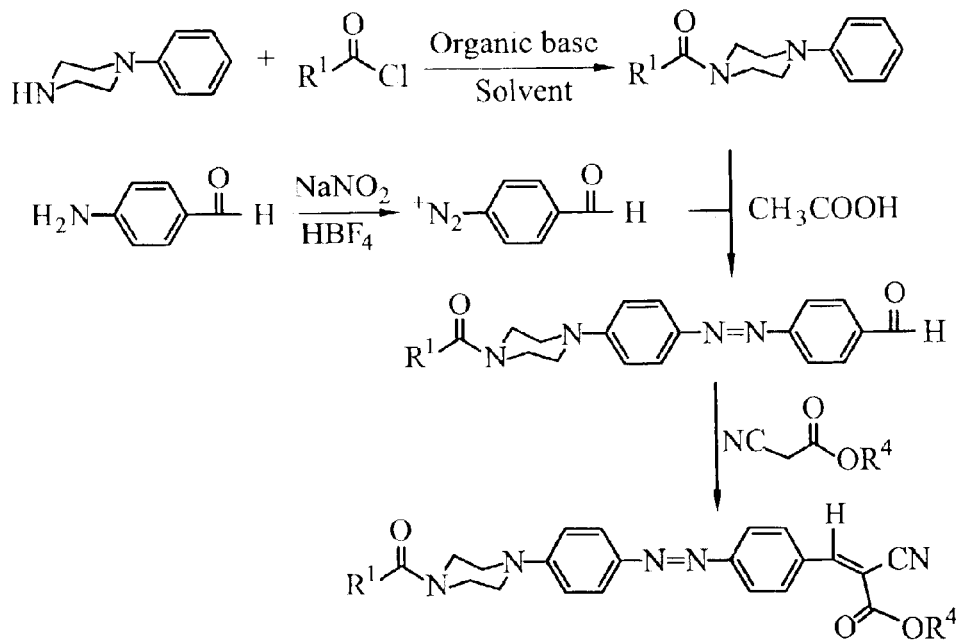

Referring to FIG. 1b for the preparation of the orange dichroic dye of the present invention, R$^1$ and R$^4$ are defined as mentioned above. Phenylpiperazine and alkanoyl chloride are dissolved in a non-polar solvent, such as methylene chloride. An organic base, such as $Et_3N$, is added to the resulting solution in an ice bath to form a phenylpiperazine derivative. Separately, poly(aminobenzaldehyde) reacts with sodium nitrite and $HBF_4$ at 0° C. to form a diazonium salt. Then, the diazonium salt and the above phenylpiperazine derivative are allowed to react in acetic acid at room temperature, forming an N,N-disubstituted-4-aminophenylazobenzaldehyde, which is allowed to react with cyano-acetic acid alkyl ester in ethanol at 80° C., forming an azophenyl cyano acid alkyl ester having a piperazinyl group as shown in FIG. 1b, an orange dichroic dye.

Figure 1C:
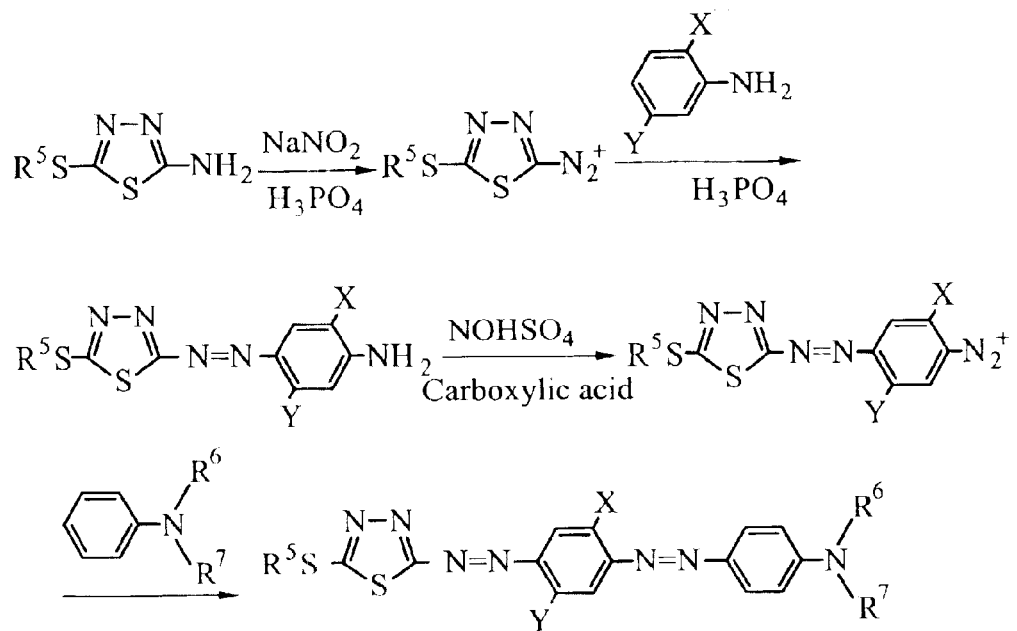

Referring to FIG. 1c for the preparation of the red dichroic dye of the present invention, $R^5$, $R^6$ and $R^7$ are defined as mentioned above. 2-amino-5-alkylthio-1,3,4-thiadiazole (wherein the alkyl is, for example, methyl or ethyl) is dissolved in phosphorous acid, cooled at 0~-5° C. in an ice bath, and allowed to react with sodium nitrite. At the same temperature, an aniline reactant (such as 2,5-dimethyl aniline) is further added, forming a product. The product is dissolved in carboxylic acid, cooled at 0~-5° C. in an ice bath, and, to the resulting solution, a solution of nitrosyl-sulfuric acid in concentrated sulfuric acid is slowly added, forming a diazonium salt. The diazonium salt is further allowed to react with an aniline reactant having substitutes on the nitrogen atoms (such as, N-methyl-N-octylaniline), forming an azo compound having a thiadiazole group as shown in FIG. 1c, a red dichroic dye.

The present invention still provides a compound having formula (V):

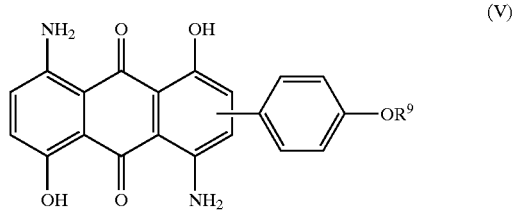

(V)

wherein $OR^9$ is $OC_4H_8F$,

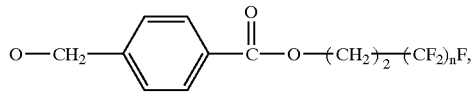

or

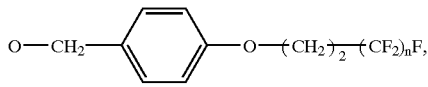

wherein n is an integer of 1 to 10. Preferably, $OR^9$ is

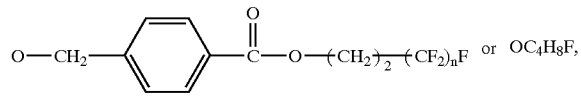

wherein n is an integer of 1 to 6. The compound having formula (V) is a novel blue dichroic dye.

Figure 1D:
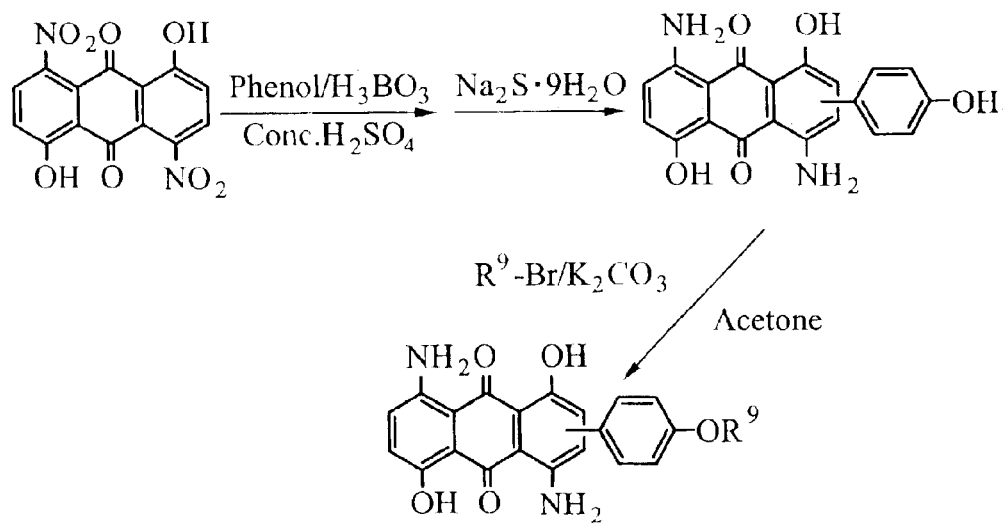

Referring to FIG. 1d for the preparation of the blue dichroic dye, $R^9$ are defined as mentioned above. 1,5-dihydroxy-4,8-dinitroanthraquinone and $H_3BO_3$ are dissolved in concentrated sulfuric acid and allowed to react with phenol at a temperature between -5° C. and -10° C. The product is collected and dissolved in a solvent (such as acetone), then, potassium carbonate and 1-halo-alkane (may have a fluoride substitute, for example, 1-bromo-4-fluorobutane) are added and heated at 70° C. for reaction, forming an anthraquinone compound as shown in FIG. 1d, a blue dichroic dye.

In the dichroic dye of the present invention, the compound having formula (II) exhibits yellow color, the compound having formula (III) exhibits orange color, the compound having formula (IV) exhibits red color, and the compound having formula (V) exhibits blue color. Accordingly, they can be combined in an appropriate ratio to form a composition of a desired color. For example, a black dichroic dye composition can be formed by mixing 0.2~0.25 g of yellow dichroic dye ($UV_{max}$_380~420 nm), 0.24~0.28 g of orange dichroic dye ($UV_{max}$_420~460 nm), 0.26~0.3 g of red dichroic dye ($UV_{max}$_510~550 nm), and 0.38~0.45 g of blue dichroic dye ($UV_{max}$_590~640 nm).

The novel azo and anthraquinone compound dichroic dyes of the present invention can be combined with a nematic liquid crystal, smetic liquid crystal, or cholesteric liquid crystal compound to form a novel guest-host mode dichroic dye liquid crystal composition. The dichroic dye and the liquid crystal compound can be combined in a ratio so that the dye is 0.5%~3% by weight, preferably 1%~3% by weight, and most preferably 2.5%~3% based on the weight of liquid crystal.

The novel guest-host mode dichroic dye liquid crystal composition can be utilized in the transmissive, trans-flective, and reflective liquid crystal display element in the active or passive driver module by the conventional art, forming the liquid crystal display element of the present invention.

Figure 4:
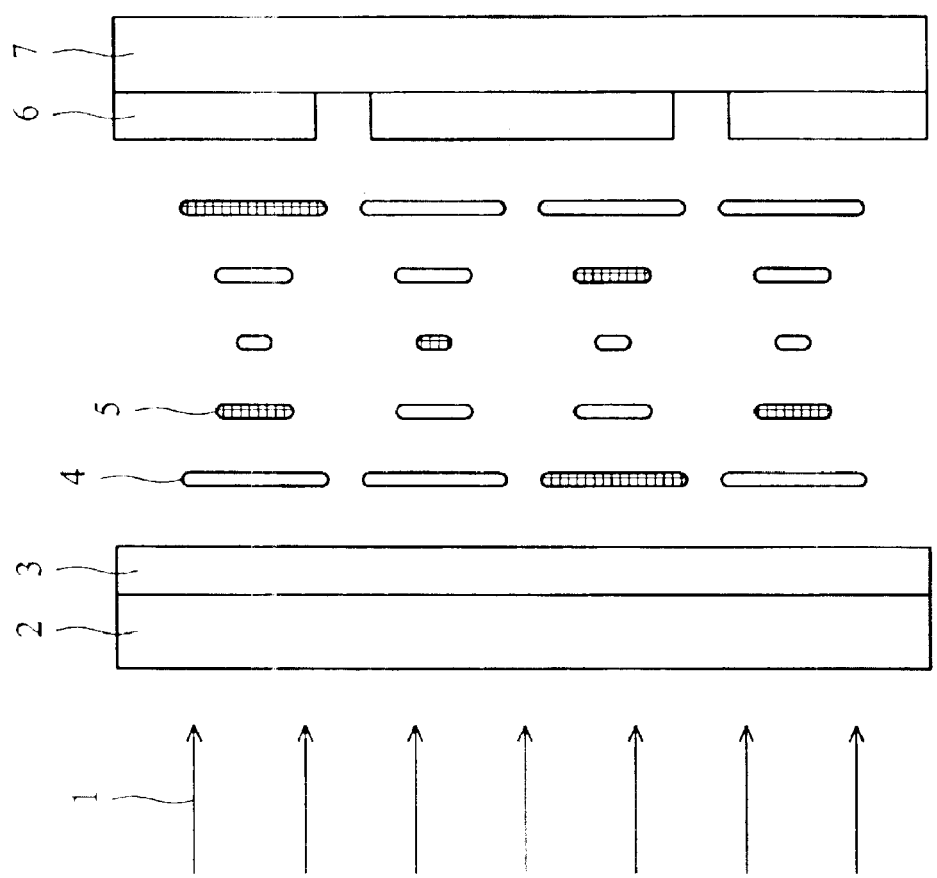
FIG. 4 is a schematic cross section of the reflective guest-host mode liquid crystal display element of the present invention when the voltage is not applied to liquid crystal layer.
Figure 5:
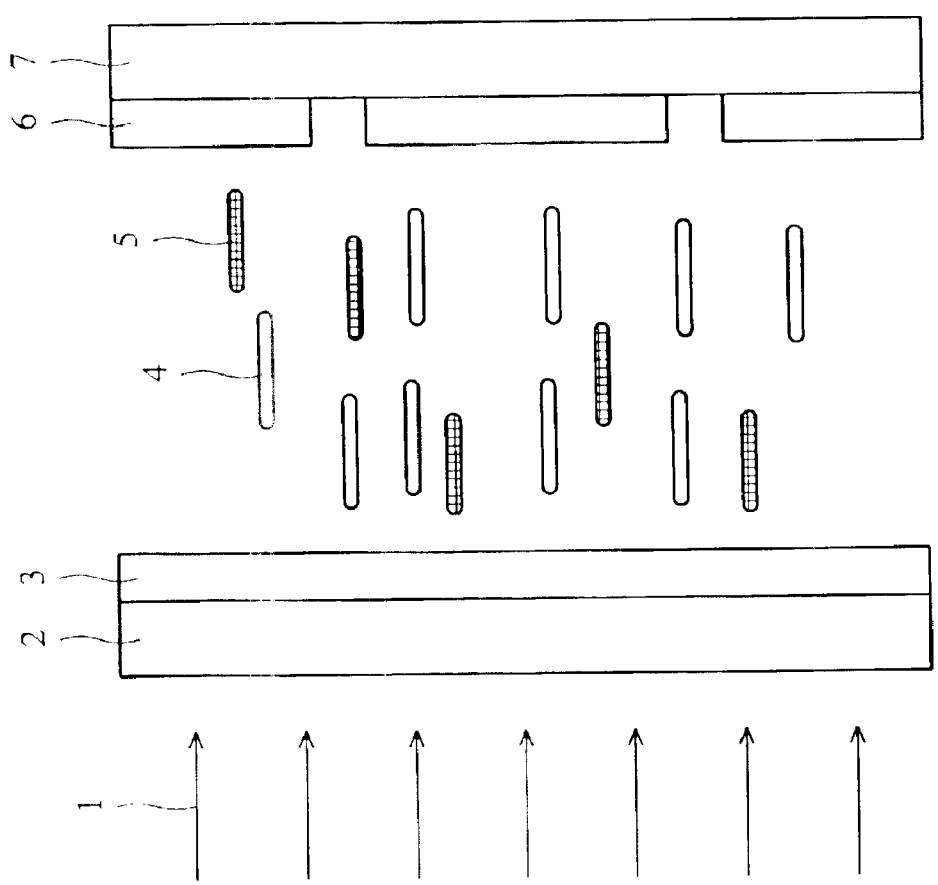
FIG. 5 is a schematic cross section of the reflective guest-host mode liquid crystal display element of the present invention when the voltage is applied to the liquid crystal layer.

The liquid crystal display element of the present invention is further described by the illustrations of FIGS. 4 and 5. A guest-host liquid crystal composition containing the dichroic dye of the present invention is placed in the liquid crystal cell of a reflective liquid crystal display element. In the Figures, reference numeral 1 indicates an incident light, numeral 2 a transparent glass plate, numeral 3 a transparent electrode, numeral 4 a liquid crystal compound, numeral 5 dichroic dyes, numeral 6 a reflective electrode, and numeral 7 a substrate. FIG. 4 shows that the liquid crystal compound 4 and dichroic dyes 5 together exhibit a cholesteric phase, whereby the incident light 1 which may be natural light, will be absorbed by the dyes 5, and thus the display exhibits a black color. When a voltage is applied (FIG. 5), the liquid crystal compound 4 and the dichroic dyes 5 align in the direction of the electric field, whereby the light 1 passes through the liquid crystal layer and reflected by the reflective electrode 6 or reflected substrate 7, and thus the display exhibits brightness.

EXAMPLE 1
Synthesis of Yellow Dichroic Dye 1.5 g of Hexanoyl chloride was added dropwise slowly into a round-bottom flask charged with 1.62 g of phenylpip-erazine and 20 ml of $CH_2Cl_2$ in an ice bath, immediately followed by 1.32 g of slowly added $ET_3N$. The resulting mixture was stirred for 30 minutes at 0° C., and 2 hours at room temperature for a complete reaction, and, then, subjected to extraction with water and $CH_2Cl_2$, and washed with diluted hydrochloric acid. The resulting organic layer was dried over anhydrous $MgSO_4$ and the solvent was removed by vacuum, giving a product, i.e. phenylpiperazine derivative, in a 75% yield.

1.93 g of 4-aminobenzoic acid butyl ester and 8 ml of 50% $HBF_4$ aqueous solution were added to a three-necked round-bottom flask equipped with a thermometer and a stirrer, and the resulting solution was diluted with 7 ml of hot water (90° C.). When the solution became transparent, it was brought to an ice bath at 0° C. and 1.03 g of NaNO₂ was slowly added, kept at temperature and stirred overnight, giving diazonium salt precipitates which were then filtered, washed with ether, and dried. The diazonium salt (2.4 mmole) was dissolved in 15 ml of acetic acid, added the phenylpiperazine derivative (2 mmole), and stirred for 2 hours for a complete reaction. The resulting mixture was subjected to extraction with water and CH₂Cl₂, and the organic layer was collected to give a crude product which was purified by column chromatography to obtain a yellow solid, N,N-disubstituted 4-aminophenylazobenzoic acid butyl ester, a yellow dye of the present invention, in a 45.3% yield. $UV_{max}$ absorbance= 413 nm.

EXAMPLE 2
Synthesis of Orange Dichroic Dye 1.21 g of poly(aminobenzaldehyde) and 8 ml of 50% $HBF_4$ solution were charged into a three-necked round-bottom flask equipped with a thermometer and a stirrer, and diluted with 7 ml of hot water (90° C.). When the resulting solution became transparent, it was cooled at 0° C. in an ice bath. Then, 1.03 g of NaNO₂ was added with the temperature maintained and stirred overnight. Precipitates of diazonium salt were obtained by filtering, washed with ether, and dried. 2.4 mmole of the diazonium salt was dissolved in 10 ml of acetic acid, 2 mmole of phenylpiperazine derivative obtained from example 1 was added, and stirred for 2 hours. After the reaction was completed, an extraction was effected with water and CH₂Cl₂, and the organic layer was collected and the crude product was purified by column chromatography, giving N,N-disubstituted-4-aminophenylazobenzaldehyde in a 40.8% yield.

0.39 g of N,N-disubstituted-4-aminophenylazobenzaldehyde and 0.15 g of cyano-acetic acid butyl ester were charged into a round-bottom flask and 10 ml of ethanol was added. The resulting mixture was heated to reflux for 24 hours. After the reaction was completed, ethanol was evacuated. The residue was subjected to recrystallization from CH₂Cl₂/MeOH, giving butyl N,N-disubstituted-4-aminophenyl-azophenyl-2-cyano-acrylate, an orange dichroic dye of the present invention, as a red solid in a 81% yield. $UV_{max}$ absorbance=450 nm.

EXAMPLE 3
Synthesis of Red Dichroic Dye 5 g of 2-amino-5methylthio-1,3,4-thiadiazole and 50 ml of $H_3PO_4$ were charged into a three-necked round-bottom flask equipped with a thermometer and a stirrer. When the resulting solution became transparent, it was cooled at a temperature between 0° C. and −5° C. in an ice bath. Then, 2.76 g of NaNO₂ dissolved in water was added dropwise with the temperature maintained and further stirred for 2 hours after the addition was completed. Then, 4.26 g of 2,5-dimethylaniline was added dropwise with the temperature maintained below 0° C. and further stirred for 2 hours after the addition was completed. Then the solution in whole was poured into ice water and the resulting solution was adjusted to a pH between 4 and 5 with 4N $NaOH_{(aq)}$, filtered, and dried, giving a reddish purple solid. The solid was subjected to extraction with methanol. The solid dissolved in methanol was collected as a mono-azo product.

0.25 g of mono-azo product obtained from the procedure described above was dissolved in 20 ml of a mixed acetic acid/propionic acid (3:1 by volume) solvent and placed into a round-bottom flask in an ice bath at a temperature below 5° C. 3.2 g of 40% nitrosylsulfuric acid in concentrated sulfuric acid was slowly added dropwise; meanwhile the temperature is inside the flask was kept at not more than 5° C. Because the reaction was fierce, only one more hour was required to complete after the addition was finished. The result was a solution of an azo salt, and was allowed to stand and cool at a temperature below 5° C. for the next procedure.

2 g of N-methyl-N-octylaniline and 1 g of sodium acetate were charged into a round-bottom flask, 5 ml of methanol was added, and the resulting mixture was cooled in an ice bath at a temperature below 5° C. The solution of an azo salt from the preceding procedure was slowly added dropwise into the flask, meanwhile the temperature inside the flask was maintained below 5° C., and the pH of the mixture was kept between 5 and 6. If the pH was less than 5, it was adjusted to between 5 and 6 with 4 N $NaOH_{(aq)}$. The solution of an azo salt was added during the control of temperature and pH, and the reaction was completed 2 hours after the addition was completed. The result was filtered while cool, washed with water to result in a neutral brownish black solid, dried in a vacuumed oven, and then purified by column chromatography, giving {4-[2,5-dimethyl-4-(5-methylthio-[1,3,4]thiadiazole-2-yl-azo)phenylazo]phenyl}-methyl-octylamine, a red dichroic dye of the present invention as a golden solid in a 22% yield. $UV_{max}$ (toluene) absorbance=531 nm.

EXAMPLE 4
Synthesis of Blue Dichroic Dye 2 g of 1,5-dihydroxy-4,8-dinitroanthraquinone and 2.8 g of H3BO3 were charged into a round-bottom flask, 28 ml of concentrated sulfuric acid was added, and the resulting mixture was heated at 70° C. to allow H3BO3 to dissolve completely. The resulting purple solution was cooled at −10° C., and 1 g of phenol was slowly added dropwise. The inside of the flask was maintained at a reaction temperature between −5° C. and 10° C. After stirring for 2 hours, the reactant was poured into ice water, and the resulting suspension was heated and stirred to reflux for 4 hours. After cooling, the reaction mixture was filtered, washed with water to be neutral, and blue residue was collected. The undesirable by-product was removed by extraction with toluene using Soxhlet extractor. The desired product was extracted with acetone and dried in a vacuum, yielding 1 g of blue solid. 1 g of the blue solid, 8 g of $Na_2S.9H_2O$, 20 ml of water, and 1 ml of ethanol were mixed, heated at 105° C., and stirred for 6 hours. The resulting mixture was then cooled to room temperature, acidified with $HCl_{(aq)}$, filtered, and washed with water to be neutral, and blue residue was collected and dried in a vacuum oven. The dried residue was dissolved in acetone and 2 g of $K_2CO_3$ and 0.5 g of 1-Bromo-4-fluorobutane were added, and then the mixture was heated to reflux for 24 hours. After the reaction mixture was cool, $K_2CO_3$ was filtered off and the filtrate was vacuumed to dry. The residue was subjected to purification by recrystallization from a mixed solvent (CH₂Cl₂:MeOH= 1:3) or by column chromatography, giving 4,8-diamino-2-[4(4-fluoro-butoxy)-phenyl]-1,5-dihydroxylanthraquinone, a blue dichroic dye of the present invention, as a blue solid in a 10% yield. $UV_{max}$ (toluene) absorbance=630 nm.

Test and Comparison for Photostability of Dichroic Dyes
Test Method

Figure 2:
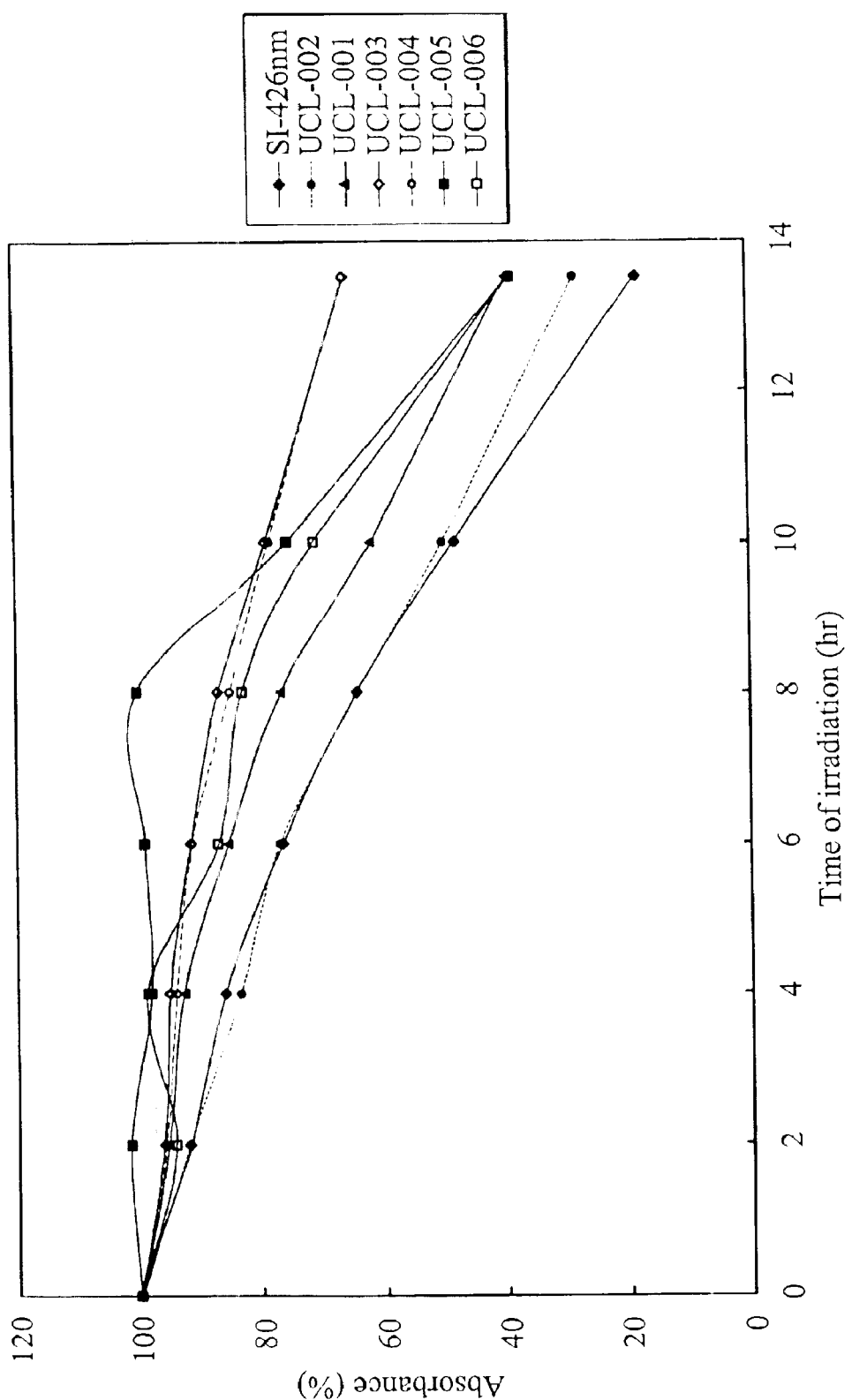
FIG. 2 is a plot of absorbance against time of irradiation for the examples UCL-001 to UCL-006 of the present invention and SI-426 nm a product of prior art.

Samples as shown in table 1 were prepared and irradiated with UV light having a wavelength of 350 nm from a UV tube, and the absorbance in the UV-visible range was measured. The absorbance was plotted against the time of irradiation for comparing the photostability of the samples. The results are shown in FIG. 2.

TABLE 1

| Sample No. | Chemical structure of sample |
|---|---|
| SI-426 | Product of Mitsui Company, Japan |
| UCL-100 | H₃CS-[thiadiazole]-N=N-[phenyl]-N=N-[phenyl]-N(CH₃)₂ |
| UCL-002 | H₃CS-[thiadiazole]-N=N-[phenyl]-N=N-[phenyl]-N(CH₃)(C₈H₁₇) |
| UCL-003 | 1-amino-4-hydroxy-5-amino-8-hydroxy-2-(4-octyloxyphenyl)anthraquinone |
| UCL-004 | anthraquinone derivative with -O-CH₂-[phenyl]-C(O)O-CH₂CH₂-Rf group |
| UCL-005 (Example 1) | C₅H₁₁-C(O)-N[piperazine]N-[phenyl]-N=N-[phenyl]-C(O)O-C₄H₉ |
| UCL-006 (Example 2) | C₅H₁₁-C(O)-N[piperazine]N-[phenyl]-N=N-[phenyl]-CH=C(CN)-C(O)-OC₄H₉ |

Test Results

As shown in FIG. 2, the dichroic dyes of the present invention (UCL-001~UCL-006) were more photostable than the comparative sample. While the anthraquinone dyes intrinsically had better photostability than azo dyes indeed in view of the results of this experiment, for azo dyes, the introduction of heterocyclic thiodiazole and piperazine groups advantageously improved the photostability.

Test and Comparison for Solubility of Dichroic Dyes
Test Method
The solubility of the compound having formula (VI) of prior art and the compound having formula (VII) of the present invention:

(VI)

-continued

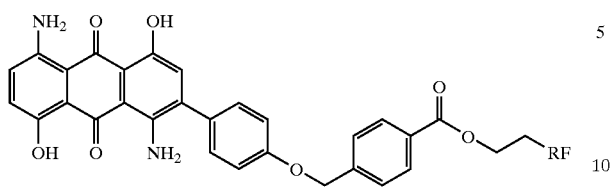

in various liquid crystals were tested, and the results are shown in Table 2.

TABLE 2

| LC Dye | ZLI-1565 | ZLI-1840 | ZLI-2452 | ZLI-5100 |
|---|---|---|---|---|
| Formula (VI) of prior art | 0.3 | 0.6 | 0.3 | 0.5 |
| Formula (VII) of the present invention | 0.5 | 1.0 | 0.7 | 0.9 |

As the data in Table 1 shows, the solubility of the compound having formula (VII) was better than that of the compound having formula (VI). The solubility was improved due to the introduction of fluorine atoms which allowed the increased compatibility between the compound having formula (VII) and F-type liquid crystal.

EXAMPLE 5

Compounds having formula $C_{27}H_{36}N_7S_2$ (yellow dichroic dye), $C_{30}H_{37}N_5O_3$ (orange dichroic dye), $C_{26}H_{35}N_7S_2$ (red dichroic dye), and $C_{24}H_{21}FN_2O_5$ (blue dichroic dye) of the present invention were mixed in a ratio of 0.5:0.5:0.4:0.9 by weight in acetone. The resulting dye mixture was dissolved in ZLI-5100-100 (Trademark, liquid crystal product sold by E. Merck, Germany) so that the weight of the dye mixture is 0.85% of the weight of the liquid crystal product, forming a full wavelength range (400~700 nm) absorption type guest-host dichroic dye liquid crystal composition. The composition exhibited black color and had an acceptable dichroic ratio and solubility in addition to excellent photostability.

Figure 3:
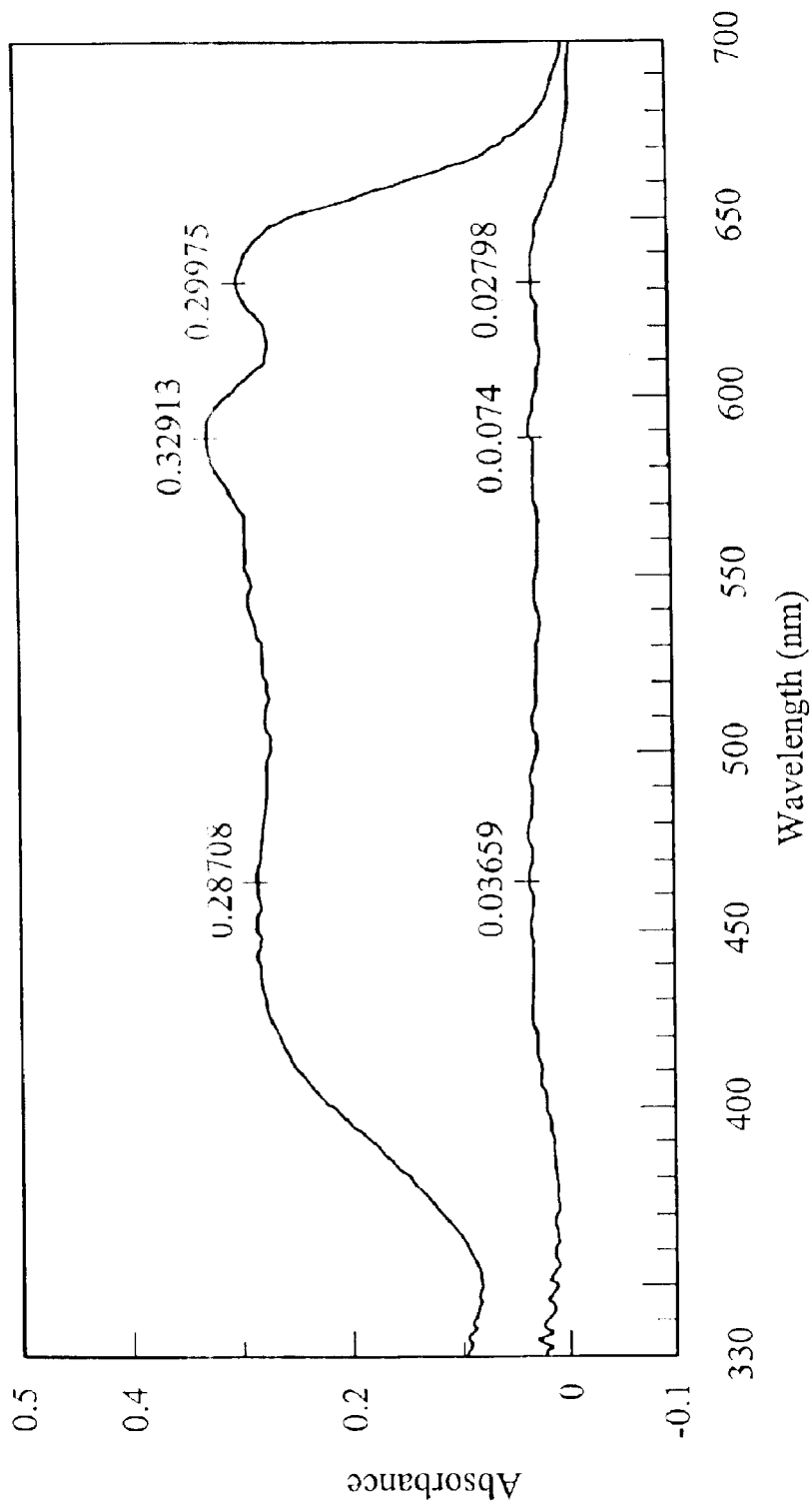
FIG. 3 is a plot of absorbance against wavelength detected for polarized light parallel to the alignment direction and for polarized light perpendicular to the alignment direction through the black dye of the present invention.

A normally black homogeneous test sample having a thickness between 6 and 8 μm was prepared from the guest-host dichroic dye liquid crystal composition just mentioned above. The test sample and a polarizer were collocated, the brightness was then determined by ELDIM. The results are shown in FIG. 3. The test sample had a good dichroic ratio (N). For example, at the wavelength of 426 nm, the dichroic ratio was 7.85 and the order parameter ($S_D$) was 0.70; at the wavelength of 580 nm, the dichroic ratio was 10.71 and the order parameter was 0.76.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A compound having formula (I):

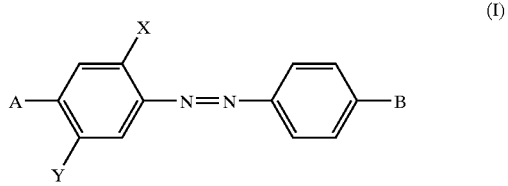

wherein

A is

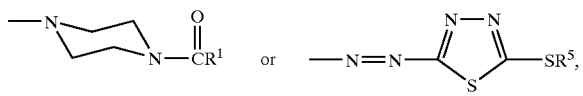

B is —CHC(CN)COOR⁴ and X and Y are both hydrogen when A is

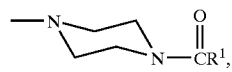

wherein $R^1$, and $R^4$ are each independently a $C_{1-10}$ alkyl group which may be substituted by one or more fluorine atoms; and B is —NR⁶R⁷ and X and Y are different and X is a $C_{1-4}$ alkyl group, and Y is Cl, Br, I, a $C_{1-4}$ alkyl group, —OCH₃, or —OC₂H₅ or X and Y, being the same, are H, Cl, Br, I, a $C_{1-4}$ alkyl group, —OCH₃, or —OC₂H₅ when A is

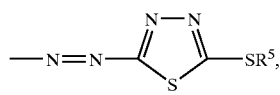

wherein $R^5$ is —CH₃ or —C₂H₅, and $R^6$ and $R^7$ are each independently a $C_{1-10}$ alkyl group, —CH₂CH₂(CF₂)ₘF,

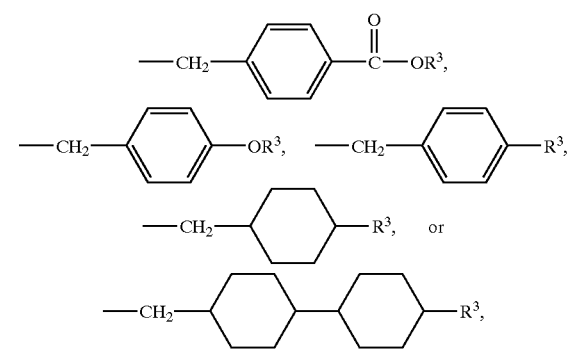

wherein m is an integer of 1 to 10 and $R^3$ is an $C_{1-4}$ alkyl group.

2. A compound having formula (III):

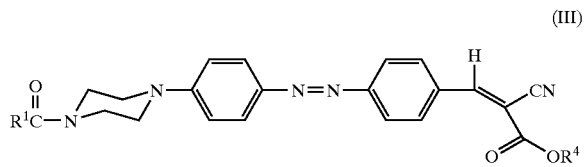

wherein $R^1$ and $R^4$ are each independently a $C_{1-10}$ alkyl group which may be substituted by one or more fluorine atoms.

3. The compound as claimed in claim 2, wherein $R^1$ is a $C_{2-8}$ alkyl group which may be substituted by one or more fluorine atoms.

4. The compound as claimed in claim 2, wherein $R^4$ is a $C_{2-8}$ alkyl group which may be substituted by one or more fluorine atoms.

5. The compound as claimed in claim 2, wherein $R^1$ is —$C_5H_{11}$ and $R^4$ is —$C_4H_9$.

6. A compound having formula (IV):

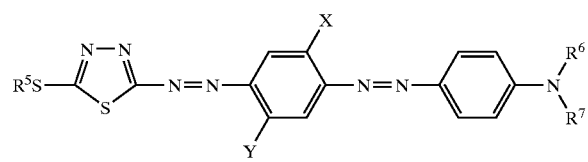

wherein
X and Y are different and X is a $C_{1-4}$ alkyl group, and Y is Cl, Br, I, a $C_{1-4}$ alkyl group, —$OCH_3$, or —$OC_2H_5$, or X and Y, being the same, are Cl, Br, I, a $C_{1-4}$ alkyl group, —$OCH_3$, or —$OC_2H_5$;
$R^5$ is —$CH_3$ or —$C_2H_5$; and
$R^6$ and $R^7$ are each independently a $C_{1-10}$ alkyl group, —$CH_2CH_2(CF_2)_mF$,

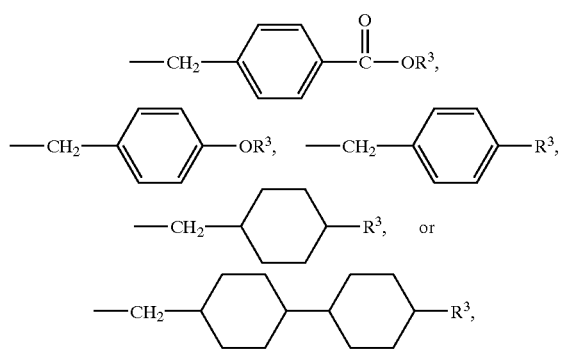

wherein m is an integer of 1 to 10 and $R^3$ is a $C_{1-4}$ alkyl group.

7. The compound as claimed in claim 6, wherein X is a $C_{1-4}$ alkyl group.

8. The compound as claimed in claim 6, wherein Y is a $C_{1-4}$ alkyl group.

9. The compound as claimed in claim 6, wherein $R^6$ is a $C_{1-2}$ alkyl group.

10. The compound as claimed in claim 6, wherein $R^7$ is a $C_{1-10}$ alkyl group.

11. The compound as claimed in claim 6, wherein X is methyl, Y is methyl, $R^6$ is methyl, and $R^7$ is —$C_8H_{17}$.

12. A compound having formula (V):

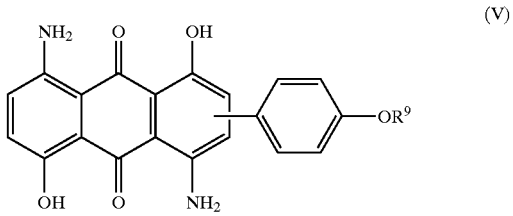

wherein $OR^9$ is $OC_4H_8F$,

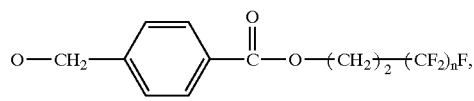

or

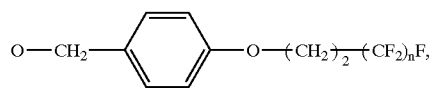

wherein n is an integer of 1 to 10.

13. The compound as claimed in claim 12, wherein $OR^9$ is $OC_4H_8F$ or

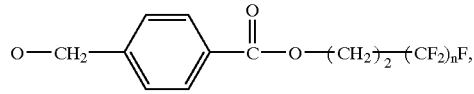

wherein n is an integer of 1 to 6.

14. The compound as claimed in claim 13, wherein $OR^9$ is $OC_4H_8F$.

15. A composition of dichroic dyes, which includes a compound selected from the group consisting of a compound having formula (I):

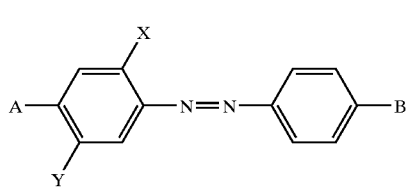

wherein
A is

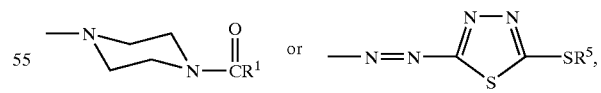

B is —$CHC(CN)COOR^4$ and X and Y are both hydrogen when A is

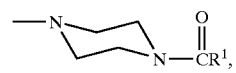

wherein $R^1$, and $R^4$ are each independently a $C_{1-10}$ alkyl group which may be substituted by one or more fluoride atoms; and B is —NR$^6$R$^7$ and X and Y are different and X is a C$_{1-4}$ alkyl group, and Y is Cl, Br, I, a C$_{1-4}$ alkyl group, —OCH$_3$, or —OC$_2$H$_5$ or X and Y, being the same, are H, Cl, Br, I, a C$_{1-4}$ alkyl group, —OCH$_3$, or —OC$_2$H$_5$ when A is

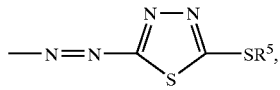

wherein R$^5$ is —CH$_3$ or —C$_2$H$_5$, and R$^6$ and R$^7$ are each independently a C$_{1-10}$ alkyl group, —CH$_2$CH$_2$(CF$_2$)$_m$F,

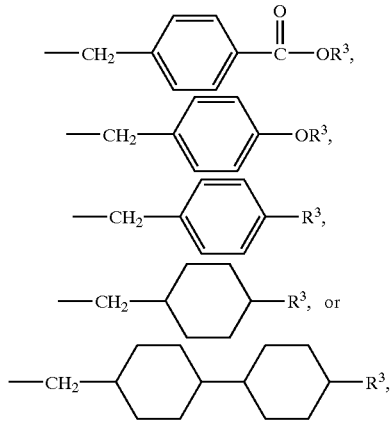

wherein m is an integer of 1 to 10 and R$^3$ is an C$_{1-4}$ alkyl group;

and a compound having formula (V):

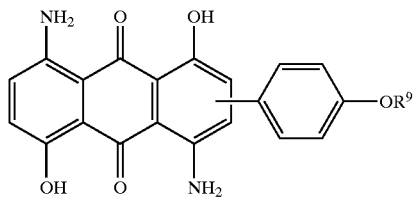

wherein OR$^9$ is OC$_4$H$_8$F,

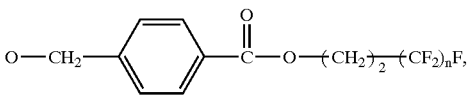

or

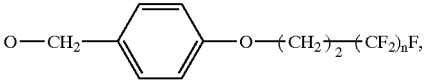

wherein n is an integer of 1 to 10.

16. The composition as claimed in claim 15, which is a black dichroic composition.

17. A dichroic dye liquid crystal composition, which includes liquid crystal compounds and the compound as claimed in claim 1 or 12.

18. The dichroic dye liquid crystal composition as claimed in claim 17, wherein the liquid crystal is selected from the group consisting of nematic liquid crystal, smetic liquid crystal, and cholesteric liquid crystal.

19. A liquid crystal display element, which includes the compound as claimed in claim 1 or 12.

20. The liquid crystal display element as claimed in claim 19, wherein the driver module used in the liquid crystal display element is active.

21. The liquid crystal display element as claimed in claim 19, wherein the drive module used in the liquid crystal display element is passive.

22. The liquid crystal display element as claimed in claim 19, wherein the liquid crystal display element is transmissive.

23. The liquid crystal display element as claimed in claim 19, wherein the liquid crystal display element is transflective.

24. The liquid crystal display element as claimed in claim 19, wherein the liquid crystal display element is reflective.

* * * * *